United States Patent [19]
MacCoss et al.

[11] Patent Number: 5,137,876
[45] Date of Patent: Aug. 11, 1992

[54] NUCLEOSIDE ANTIVIRAL AND ANTI-INFLAMMATORY COMPOUNDS AND COMPOSITIONS AND METHODS FOR USING SAME

[75] Inventors: Malcolm MacCoss, Freehold; Laura C. Meurer, North Plainfield; Richard L. Tolman, Warren, all of N.J.

[73] Assignee: Merck & Co., Inc., Rahway, N.J.

[21] Appl. No.: 596,846

[22] Filed: Oct. 12, 1990

[51] Int. Cl.$^5$ ............... A61K 31/00; C07H 19/00
[52] U.S. Cl. ................... 514/23; 514/43; 536/1.1; 536/18.4; 536/18.7; 536/22; 536/23; 536/55; 536/117; 536/121
[58] Field of Search ........... 536/55, 18.4, 117, 23, 536/22; 514/43, 23

[56] References Cited

U.S. PATENT DOCUMENTS

| | | | |
|---|---|---|---|
| 4,148,888 | 4/1979 | Cantoni et al. | 424/180 |
| 4,309,419 | 1/1982 | Wolberg et al. | 424/180 |
| 4,322,411 | 3/1982 | Vinegar et al. | 424/180 |
| 4,690,917 | 9/1987 | Knight et al. | 536/55 |

FOREIGN PATENT DOCUMENTS

| | | |
|---|---|---|
| 0038567 | 4/1981 | European Pat. Off. |
| 0038568 | 4/1981 | European Pat. Off. |
| 0190726 | 4/1986 | European Pat. Off. |
| 0286418 | 4/1988 | European Pat. Off. |

OTHER PUBLICATIONS

J. P. Bader et al., 3-Deazaadenosine, and Inhibitor of Adenosylhamocysteine Hydrolase; Virology 89, 494 (1978).
A. J. Bodner et al., Antiviral Acitivty of 3-Deazaadenosine and ..., Biochem, and Biophysic. Res. Comm., 98, 476 (1981).
P. A. Bonnet et al., N-Nitro and N-Nitroso derivatives in 5, 6, 7, 8 Tetrahydro ..., J. Chem. Res., 1984, 28.
P. K. Chaing and G. L. Cantoni, Perturbation of Biochemical Transmethylations ..., Biochem. Pharmac., 28, 1897 (1979).
P. K. Chaing et al., S-Adenosyl-L-Homocysteine Hydrolase: Analogues of S-Adenosyl ..., Mol. Pharma., 13, 939 (1977).
M. F. DePompei and W. W. Paudler, The Synthesis and Some Chemical and Spectroscopic Properties, J. Heterocycl. Chem., 12, 861 (1975).
W. C. Luma and J. P. Springer, Novel Condensation of 2,3-Epoxybutanal ..., J. Org. Chem., 46, 3735 (1981).
T. A. Krenitsky et al., Imidazo [4,5-c]pyridines (3-Deazapurines) and ..., J. Med. Chem., 29, 138 (1986).
C. Levallois et al., Theophylline-like Properties of Xanthine Analogs, Biochem. Pharmaco., 33, 2253 (1984).
C. Sablayrolles et al., Synthesis of Imidazo [1,2-a] Pyrazine Derivatives ..., J. Med. Chem., 27 206 (1984).
C. M. Stoltzfus and J. A. Montgomery, Selective Inhibition of Avian ..., J. Virology 38, 173 (1981).
J. C. Teulade et al., C-3 Hydroxylation of some Imidazo [1,2-a]azines, J. Chem. Res. 1986, 202.
W. Trager et al., Plasmodium Falciparum: Antimalarial Activity ..., Exp. Parasit., 50, 83 (1980).
B. Veroek et al., Hydrazinolysis of some asolopyrazines, Heterocycles, 4, 943 (1976).
W. E. Coyne, "Nonsteroidal Antiinflammataory Agents", Medicinal Chemistry (ed. A. Burger) p. 953 (Wiley-Interscience).
G. D. Diana et al., "Antiviral Agents", Annual Reports in Medicinal Chemistry, 24, p. 129 (1989).
Mitsuya et al., Japan Sci. Soc. Press Tokyo, Japan pp. 227–288 (1985).
Sandstshi et al., Review article in Drugs, 34, pp. 373–390 (1987).

Primary Examiner—Johnnie R. Brown
Assistant Examiner—T. Oliver Wilson
Attorney, Agent, or Firm—Charles M. Caruso; Roy D. Meredith; David A. Muthard

[57] ABSTRACT

The compound having the formula:

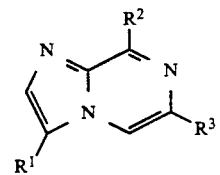

has antiviral activity, specifically in the prevention or treatment of infection by retroviruses, including HIV, and immunosuppressive activity, either as a compound, pharmaceutically acceptable salt, or a pharmaceutical composition ingredient, whether or not in combination with other antivirals, immunomodulators, antibiotics or vaccines. Methods of preventing or treating viral infections and modulating immune responses in vivo are also described.

12 Claims, No Drawings

NUCLEOSIDE ANTIVIRAL AND ANTI-INFLAMMATORY COMPOUNDS AND COMPOSITIONS AND METHODS FOR USING SAME

BACKGROUND OF THE INVENTION

The present invention is concerned with compounds and their pharmaceutically acceptable salts which have anti-viral activity, particularly activity against retroviruses including human immunodeficiency virus (HIV). The compounds of the present invention also act as immunomodulators. It also relates to pharmaceutical compositions containing the compounds and to a method of use of the present compounds and other agents for the treatment of viral infections and AIDS.

Retroviruses refer to a family of viruses which have RNA as their genetic material and also the enzyme reverse transcriptase (RNA-dependent DNA polymerase), of which the latter is essential for self-replication by synthesizing complementary DNA on the template RNA of the virus.

Retroviruses include various oncoviruses such as avian leukemia virus, avian sarcoma virus, avian reticuloendotheliosis virus, murine mammary cancer virus, murine leukemia virus, murine sarcoma virus, guinea pig type C virus, hamster type C virus, rat leukemia virus, feline leukemia virus, feline sarcoma virus, feline type C virus, ovine leukemia virus, bovine leukemia virus, swine type C virus, simian leukemia virus, Mason-Pfizer virus, simian sarcoma virus, simian T-lymphotropic virus, baboon type C virus, and the like. Among those infective to humans, those important are adult T-cell leukemia virus (ATLV), or human T-lymphotropic virus type I (HTLV-I) and type II (HTLV-II).

On the other hand, retroviruses also include those having no oncogenicity, such as visna virus, ovine progressive pneumonia virus, ovine maedi virus, simian T-lymphotropic virus type III (STLV-III), equine infectious anemia virus, and the like. The viruses isolated from humans as causitive agents for AIDS, ARC, PGL and LAS (so called AIDS-viruses such as HTLV-III, LAV1, LAV2, ARV and HTLV-IV) belong to this subfamily. Recently, AIDS-causative viruses are called HIVs.

Spumavirane, a subfamily of retroviruses, includes simian foaming virus. Also, a retrovirus has been recently isolated as a causative virus for Kawasaki disease (mucocutaneous lymphonode syndrome).

Hepatitis B virus (HBV) is a DNA virus with a unique circular double-stranded DNA genome which is partly single-stranded. It contains a specific DNA polymerase required for viral replication. This DNA polymerase also acts as a reverse transcriptase during the replication of HBV DNA via an RNA intermediate.

2',3'-Dideoxynucleosides and 2',3'-dideoxy-2',3'-didehydronucleosides have been shown to be effective as antiviral agents, particularly against HIV. (E. De Clercq, Adv. Druo Res., 17, 1 (1988)) 3-Deazaadenosine has also been shown to be effective as an antiviral agent (G. L. Cantoni, et al., U.S. Pat. No. 4,148,888; C. M. Stoltzfus and J. A. Montgomery, J. Vir., 38, 173 (1981); A. J. Bodner, et al., Biochem. and Biophys. Res. Comm., 98, 476 (1981)). The antiviral potential of 3-deazaadenosine has been ascribed to the compound's role as both a potent inhibitor of S-adenosylhomocysteine hydrolase and as a substrate for the same enzyme. Such a method of action causes undesirable side effects, such as general cytotoxicity.

3-Deazaadenosine and its derivatives have also been shown to inhibit the immune response and to possess antiinflamatory activity (U.S. Pat. No. 4,309,419). Similar antiinflamatory and immunosuppressant activity has been disclosed for certain 2'-deoxynucleosides (E.P. Application 0 038 569).

3-Deazaadenosine, 2',3'-dideoxynucleosides and related compounds undergo facile in vivo metabolic cleavage of their glycosyl bond, which effectively inactivates their biological potency. Adenosine derivatives such as those disclosed in U.S. Pat. No. 4,148,888 are also catabolized in vivo by deaminase enzymes.

The compounds of the instant invention retain the antiviral and immunosuppressant potency present in the nucleoside compounds that have been previously disclosed. However, unlike the previously disclosed agents, the compounds of the instant invention are not susceptable to acid or enzymatic cleavage of the labile glycosyl group.

A further advantage of the compounds of the instant invention is that they have antiviral potency without inhibiting or acting as a substrate for S-adenosylhomocysteine hydrolayse.

SUMMARY OF THE INVENTION

The present invention provides novel compounds of Formula I:

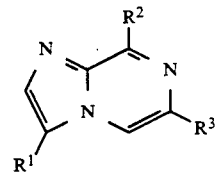

wherein $R^1$ is selected from
a)

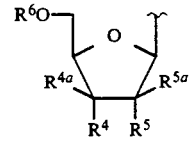

wherein
$R^4$, $R^{4a}$, $R^5$ and $R^{5a}$ are independently: hydrogen, fluorine or hydroxyl;
$R^6$ is hydrogen, $-C(O)R^7$, or

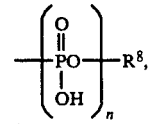

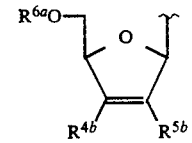

or $R^6$ may be combined with $R^4$ to form a cyclic phosphate;

wherein $R^7$ is lower alkyl;

$R^8$ is hydrogen and lower alkyl;

n is 1 to 3;

or b)

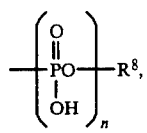

wherein $R^{4b}$ and $R^{5b}$ are hydrogen or $C_1$-$C_4$ lower alkyl;

$R^{6a}$ hydrogen, —C(O)$R^7$, or

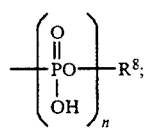

wherein $R^7$, $R^8$ and n are as defined hereinabove;

$R^2$ and $R^3$ are independently: hydrogen, —$NH_2$ or —OH;

or a pharmaceutically acceptable salt thereof.

The term "lower alkyl" is defined as $C_1$-$C_6$ alkyl moiety and is intended to include methyl, ethyl, propyl, isopropyl, butyl, sec- and tert-butyl, pentyl, hexyl and the like. It is intended that the term "lower alkyl" includes linear and branched structures.

Some of the compounds described herein contain one or more centers of asymmetry and may thus give rise to diastereoisomers and optical isomers. The present invention is meant to comprehend such possible diastereomers as well as their racemic and resolved optically active forms.

Preferably $R^6$ and $R^{6a}$ are hydrogen.

Preferably $R^2$ is —$NH_2$ or —OH when $R^3$ is hydrogen; and $R^2$ is —OH or —$NH_2$ when $R^3$ is —$NH_2$.

The following formulae further illustrate the compound of Formula I when $R^6$ is combined with $R^4$ or $R^{4a}$ to form a cyclic phosphate:

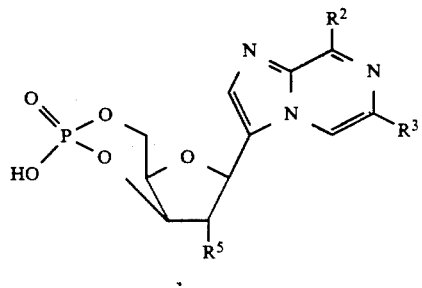

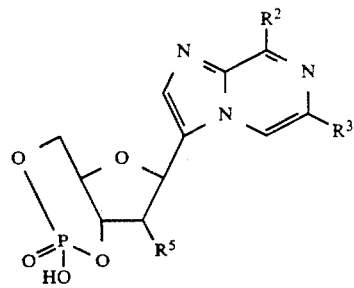

With regard to all of the preferred substituents described above, the following compounds are preferred embodiments of the present invention, but do not act to limit the present invention.

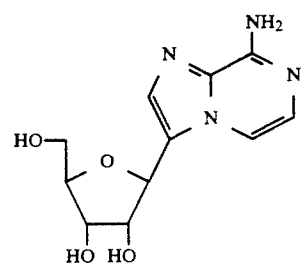

Ia

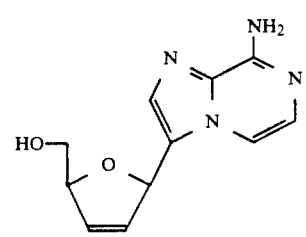

Ib

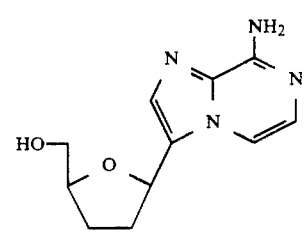

Ic

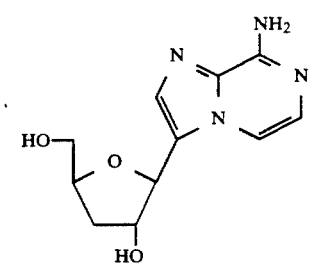

Id

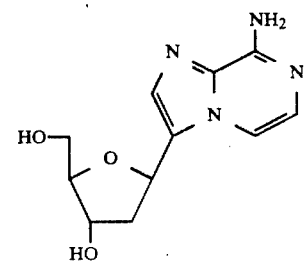

Ie

The free compound, pharmaceutically-acceptable salt or salts of the compounds of Formula I (in the form of water- or oil- soluble or dispersible products) include the conventional non-toxic salts or the quaternary ammonium salts of these compounds, which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3 phenyl-propionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucosamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

It is understood that the instant invention also discloses derivatives of the compounds of the instant invention which contain biologically labile bonds which may be cleaved under particular conditions to release the parent compound. These derivatives, also known as prodrugs, are readily converted to the compounds of the instant invention by acidic or enzymatic degradation upon administration to the mammal in need of antiviral treatment and are therefore pharmaceutical equivalents of the compounds of the instant invention. Among the derivatives of the compounds of the instant invention which may function in this capacity are carboxylic acid esters and amides, phosphate diesters and pyrophosphate diesters. Typical examples of prodrugs which have been utilized in the area of nucleoside analogs are discussed by M. MacCoss and M. J. Robins, "Anticancer pyrimidines, pyrimidine nucleosides and prodrugs" in *The Chemistry of Antitumor Agents*, pp 261-298, ed. D. E. V. Wilman, Blackie & Son Ltd., Glasgow, 1989. It is understood that the compound types discussed therein are only representative and in no way limits the derivatives that may be employed as prodrugs.

Antiviral and immunosuppressant agents of Formula I may be prepared in accordance with well-known procedures in the art. Particularly useful are the following synthetic schemes. The schemes illustrate syntheses of compounds of Formula I wherein $R^2$ is $NH_2$ and $R^3$ is H. These schemes are meant to be illustrative and are not meant to be limiting. It is understood that compounds of the Formula I wherein $R^2$ and $R^3$ are other groups as defined hereinabove may be prepared by similar synthetic procedures using appropriate starting materials.

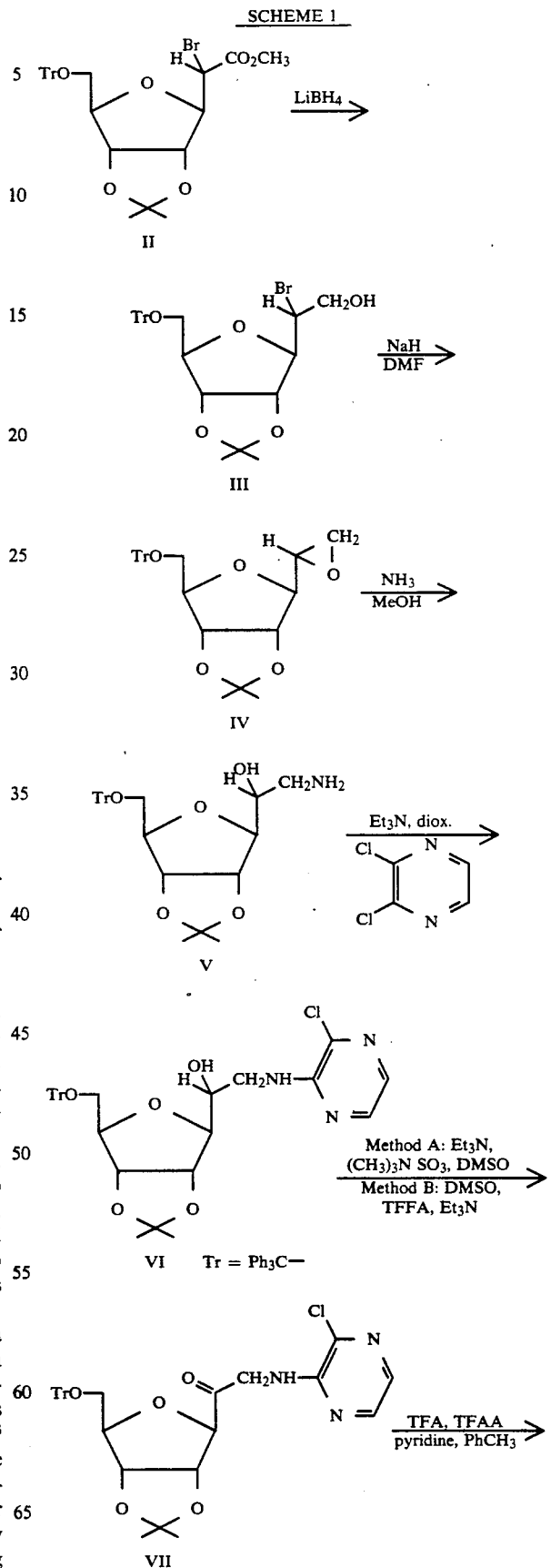

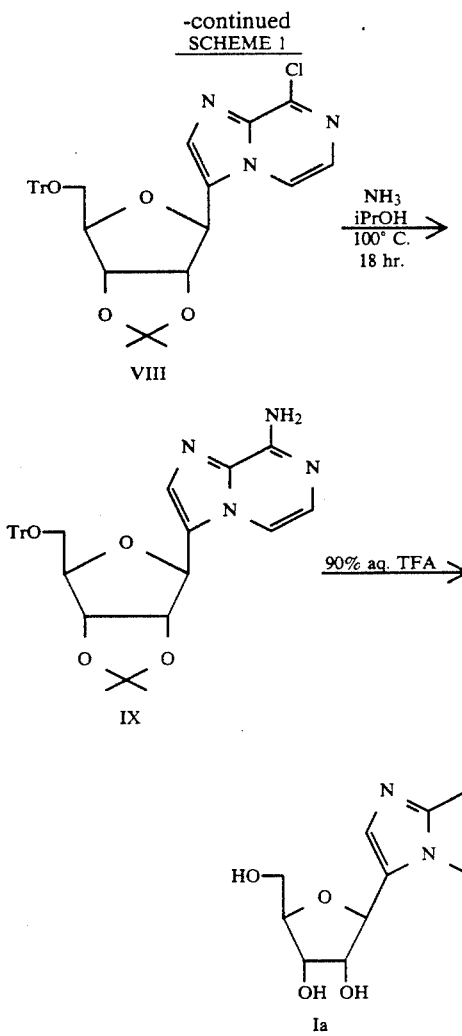

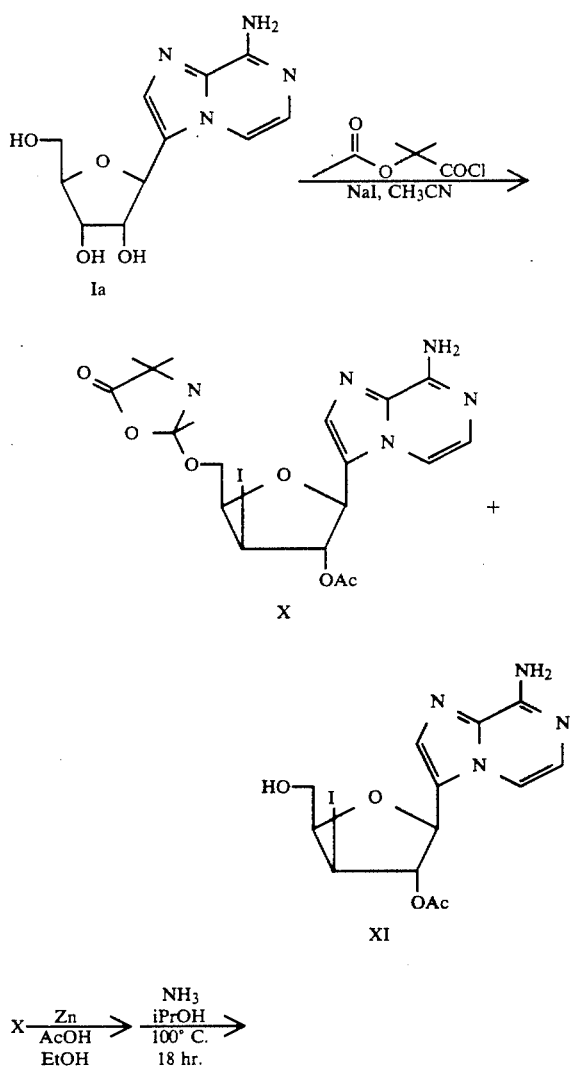

sense of pyridine in a suitable solvent, such as toluene, to provide the imidazo[1,2-a] pyrazine VIII by dehydrative cyclization.

It may then be necessary to convert a precursor moiety present in compound VIII (for example, the chloride group illustrated in Scheme 1) into the desired $R^2$ and/or $R^3$ substituent (for example $R^2=NH_2$ in Scheme 1). To this end compound VIII is treated with ammonia in isopropanol at elevated temperatures to provide the protected compound IX. The protecting groups are then removed by treating compound IX with a strong acid, such as trifluoroacetic acetic acid, in a suitable solvent, such as water, to provide compound Ia.

Scheme 2 shows the preparation of compounds of the instant invention wherein $R^1$ is group a) and $R^4=R^5=R^{4a}=R^{5a}=R^6=H$; or $R^1$ is group b) and $R^{4b}=R^{5b}=R^{6a}=H$. The scheme is intended to be illustrative and is not meant to be limiting.

The tris-protected furanosylmethylacetate II is prepared by the method described by M. C. Clingerman and J. A. Secrist, *J. Org. Chem.*, 48, 1341(1981). The ester II is then treated with a reducing agent, such as lithium borohydride, lithium aluminum hydride and the like in a suitable solvent, such as ethyl ether, tetrahydrofuran (THF) and the like, to provide the alcohol III. Treatment of the alcohol III with a proton abstractor, such as sodium hydride, lithium diisopropylamide and the like, in a suitable solvent such as dimethylforamide (DMF), THF and the like, provides the furanosyl epoxide IV. The epoxide ring is then selectively cleaved by treating compound IV with methanolic ammonia to provide the amine V.

The amine V is then coupled to a suitably substituted chloropyrazine, such as 2,3-dichloropyrazine, 2,5-dichloropyrazine and the like, in the presense of an organic nitrogen base, such as triethylamine, ethyldiisopropylamine and the like, in a suitable solvent, such as dioxane, acetonitrile and the like, to provide compound VI. The hydroxyl group of compound VI is oxidized to the corresponding ketone of compound VII by treating compound VI with an oxidizing agent, such as the combination of triethylamine, trimethylamine-sulfur trioxide and dimethylsulfoxide, the combination of triethylamine, trifluoroacetic anhydride and dimethylsulfoxide and the like. Compound VII is then treated with trifluoroacetic acid and trifluoroacetic anhydride in the pre- -continued
SCHEME 2

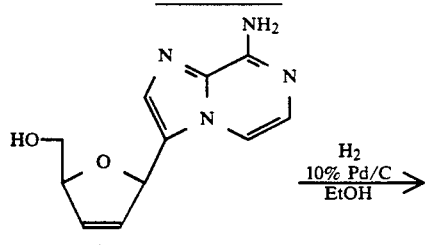
Ib

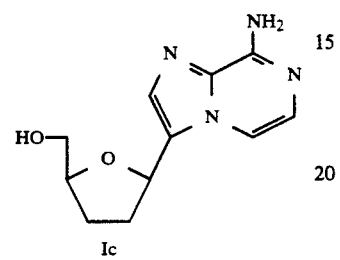
Ic

Compound Ia is treated with 2-acetoxyisobutyryl chloride (ref. T. C. Jain et al., *J. Org. Chem.*, 39, 30(1974)) to provide a 1:5 mixture of the dioxalone X and the iodo nucleoside XI. Compound X is then treated with zinc dust in the presense of an acid, such as acetic acid and the like, in a suitable solvent, such as ethanol and the like. The crude product from the reaction is then treated with ammonia in a suitable solvent, such as isopropanol and the like, at elevated temperatures in the range of 80°–120° C., to provide a compound of the instant invention, the dihydrofuranylimidazopyrazine Ib.

Compound Ib may subsequently be reduced by hydrogenation over a suitable catalyst, such as 10% palladium on carbon, platinum oxide and the like, in a suitable solvent such as ethanol and the like, to provide a compound of the instant invention Ic.

Scheme 3 shows the preparation of the compound of the instant invention wherein R¹ is group a) and R⁴=R⁴ᵃ=R⁵ᵃ=H and R⁵=—OH. The scheme is intended to be illustrative and is not meant to be limiting.

SCHEME 3

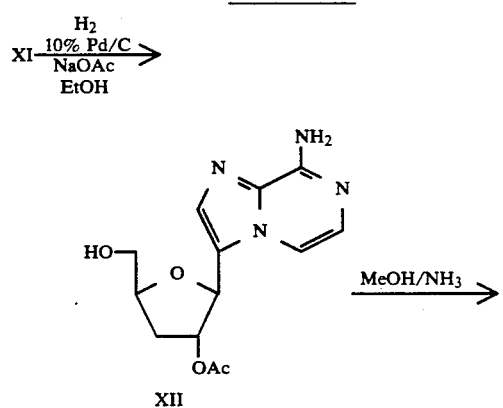

-continued
SCHEME 3

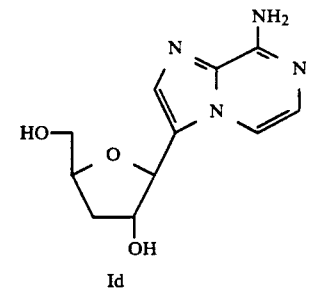
Id

Compound XI is dehalogenated by hydrogenation over a suitable catalyst, such as 10% palladium on carbon, platinum oxide and the like, in a suitable solvent, such as ethanol and the like, and optionally, in the presense of a mild base, such as sodium acetate and the like, to provide the 2'-acetoxy-3'-deoxy-β-D-ribofuranosyl nucleoside derivative XII. The acetyl group on compound XII is cleaved by treatment with methanolic ammonia to provide compound Id, a compound of the instant invention.

Scheme 4 shows the preparation of the compound of the instant invention wherein R¹ is group a) and R⁴ᵃ=R⁵=R⁵ᵃ=H and R⁴=-OH. The scheme is intended to be illustrative and is not meant to be limiting.

SCHEME 4

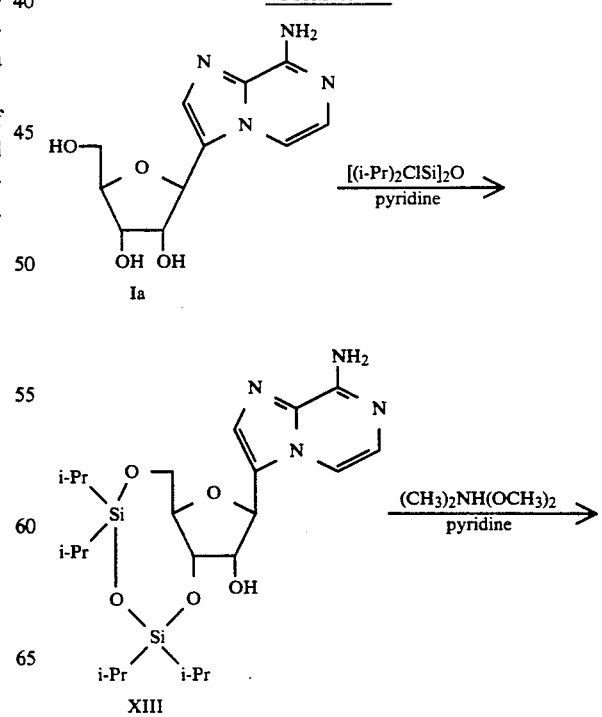

-continued
SCHEME 4

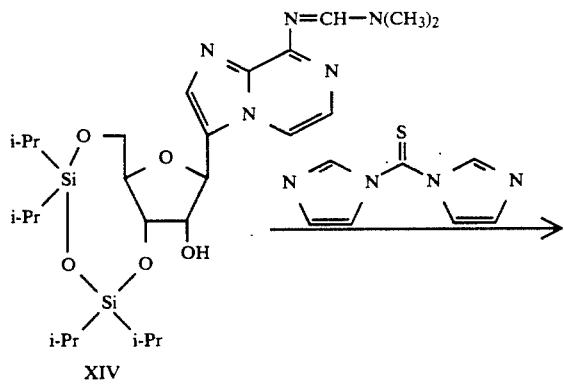

XIV

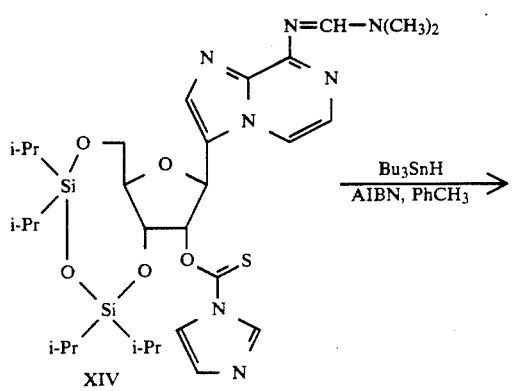

XIV

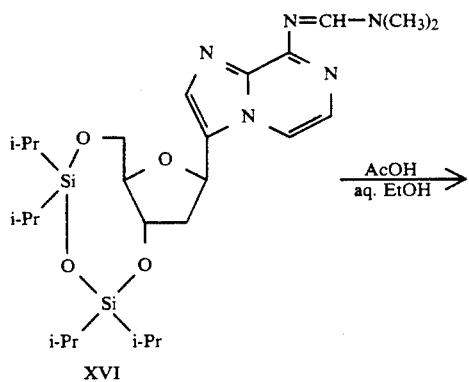

XVI

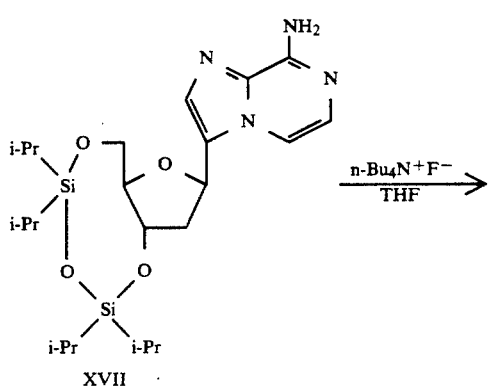

XVII

-continued
SCHEME 4

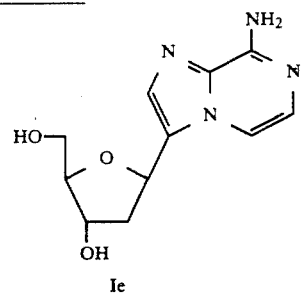

Ie

Compound Ia is treated with a bifunctional disilyl ether reagent such as bis(diisopropylchlorosilyl)ether and the like, in the presense of a base such as pyridine, triethylamine and the like, in a suitable solvent, such as pyridine, acetonitrile and the like, to provide the 3',5'-protected compound XIII. Compound XIII is then reacted with dimethylformamide dimethylacetal, in the presense of a base, such as pyridine and the like, in a suitable solvent, such as pyridine, acetonitrile and the like, to provide XIV. The remaining unblocked hydroxyl group of compound XIV is then reduced by first reacting with thiocarbonyl diimidazole or phenylchlorothionocarbonate (preferably the former) and the like, in a suitable solvent, such as DMF and the like, to provide compound XV. Reduction was then accomplished by treating compound XV with tributyltin hydride and the like, in the presense of a radical initiator, such as azabisisobutyronitrile (AIBN) and the like, in a suitable solvent, such as toluene and the like, to provide the protected 3-deoxyfuranosyl compound XVI. The protecting group of compound XVI is then hydrolized to an amine group by treating compound XVI with an acid, such as acetic acid and the like, in a suitable solvent, such as aqueous ethanol and the like, to provide compound XVII. Compound XVII is then desilylated by treating it with tetrabutylammonium fluoride in a suitable solvent, such as THF and the like, to provide a compound of the instant invention, Ie.

The compounds of the present invention are useful as anti-viral agents. The compounds are especially useful in the inhibition of HIV protease, the prevention or treatment of infection by the human immunodeficiency virus (HIV), and the treatment of consequent pathological conditions such as AIDS. Treating AIDS, preventing infection by HIV or treating infection by HIV is defined as including, but not limited to, treating a wide range of states of HIV infection: AIDS, ARC (AIDS related complex), both symptomatic and asymtomatic, and actual or potential exposure to HIV. For example, the compounds of this invention are useful in preventing infection by HIV after suspected past exposure to HIV by e.g., blood transfusion, accidental needle stick, or exposure to patient blood during surgery. The compounds of the present invention are also useful in the treatment of herpetic infections by HSV-1 and HSV-2.

The compounds of the present invention are also useful in suppressing or modulating inflammation and immunological responses and are useful therefore in the treatment of such diseases as cancer, viral infections, bacterial infections, psoriasis, an autoimmune disease (such as arthritis, systemic lupus erythematosus, inflammatory bowel disease, juvenile diabetes, myasthenia gravis, multiple sclerosis, gout and gouty arthritis), rheumatoid arthritis and rejection of transplantation.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating viral infections and especially HIV infection and AIDS. The treatment involves administering to a patient in need of such treatment a pharmaceutical composition comprising a pharmaceutical carrier and a therapeutically-effective amount of a compound of the present invention, or a pharmaceutically-acceptable salt thereof typically such therapeutically effective levels are from about 5 mg to about 250 mg per kg body weight per day.

In accordance with the present invention there is also provided a method of treating and a pharmaceutical composition for treating a human or animal in need of anti-inflammatory or immunomodualting action. The treatment involves administering to a patient in need of such treatment a pharmaceutical composition comprising a pharmaceutical carrier and a therapeutically-effective amount of a compound of the present invention, or a pharmaceutically-acceptable salt thereof. Typically such therapeutically effective levels are from about 0.3 mg to about 100 mg per kg body weight per day.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride.

The anti-inflammatory and anti-HIV action of the compounds of the instant invention are demonstrated by the results of the pharmacological tests which follow and which were carried out for evaluating the compounds according to the invention.

INHIBITION OF CARRAGEENAN-INDUCED INFLAMMATORY CELL MIGRATION IN THE RAT PLEURAL CAVITY

Specific pathogen-free Sprague Dawley rats were dosed with compound Ia ($R^3$=H) in Cremophor i.v. approximately 15 minutes before intrapleural injection with a 0.5% carrageenan in water solution. Four hours post-carrageenan injection the rats were killed with $CO_2$ and the pleural cavity contents were removed. The cells were counted by trypan blue dye exclusion. Comparison of the mean pleural cavity cell number at several dose levels of compound Ia ($R^3$=H) and the corresponding Cremophor only injection controls showed that compound Ia ($R^3$=H) had antiinflammatory activity at iv doses of 5 to 6 mg/kg.

HIV INHIBITION ASSAY

Uninfected H9 T-lymphoid cells were pre-treated for 24 hours with compound Ic at various concentrations. The cultures were then infected with HIV at a level of 1.0 infectious unit per 100 cells. Fresh analog was added every 2 to 3 days. Virus growth in the culture was determined by specific immunofluorescence. Table 1 shows the results of the assay for compound Ic as well as for the control (DMSO/water vehicle) and for 2',3'-dideoxyadenosine. The values in the table represent the percent of immunofluorescent-positive cells.

TABLE I

| Days | 12 μM | 6 μM | 3μM | 1.5 μM |
|---|---|---|---|---|
| Compound Ic: | | | | |
| 3 | 1.0 | 1.0 | 1.0 | 1.0 |
| 6 | 30.0 | 30.0 | 30.0 | 30.0 |
| 8 | 30.0 | 50.0 | 50.0 | 75.0 |
| 2',3'-Dideoxyadenosine: | | | | |
| 3 | <1.0 | <1.0 | <1.0 | <1.0 |
| 6 | <1.0 | <1.0 | <1.0 | <1.0 |
| 8 | <1.0 | <1.0 | <1.0 | <1.0 |

| 0.25 DMSO in Water vehicle: | |
|---|---|
| Days | Vehicle |
| 3 | 1.0 |
| 6 | 30.0 |
| 8 | 100.0 |

The invention is further defined by reference to the following examples, which are intended to be illustrative and not limiting. All temperatures used are in degrees Celsius.

EXAMPLE 1

8-Amino-3-(β-D-ribofuranosvl)imidazo[1,2-a] pyrazine
(Ia)

Step A:

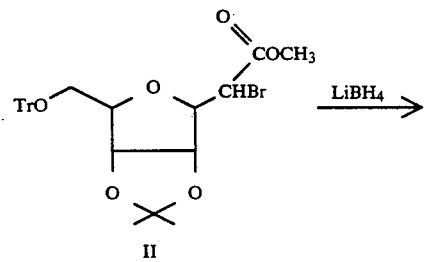

II

15

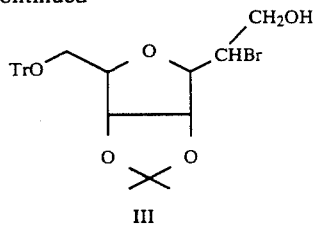

To 260 mg (11.9 mmol) of lithium borohydride in 20 mL of THF was added 5.11 g (9.03 mmol) of methyl 3,6-anhydro-2-deoxy-2-bromo-4,5-O-isopropylidene-7-O-trityl-D-allo-heptonate II while stirring in an ice bath. After 30 minutes, at 0° C. the reaction was warmed to room temperature and quenched with H₂O. The THF was evaporated and the aqueous phase was extracted twice with Et₂O. The ethereal layer was dried (MgSO₄), filtered and concentrated to provide 4.24 g (7.86 mmol, 87% of product III as an opaque oil, (a small portion, 125 mg was purified on 2 ×1000 μ silica gel prep plates (4:1 hexane: EtoAc) to give a 59 mg of a white solid).

Anal. cal. for $C_{29}H_{32}O_5Br$: C: 64:57, H: 5.59. Found. C:64.21, H:5.80.

$^1$H NMR (200 MHz CDCl₃ )δ: 1.36, 1.53, (2s, 6H, C(CH₃)2), 2.32 (m, 1H, OH), 3.26 (m, 2H, H₅, H₅'), 3.89–4.04 (m, 2H, H₁, H₄), 4.18 (m, 2H, CH₂OH) 4.21–4.29 (m, 1H, CHBr), 4.60–4.84 (m, 2H, H₂, H₃), 7.18–7.54 ppm (m, 15H, Tr).

Mass spec. FAB Li spike (m+7)=545,547.

Step B:

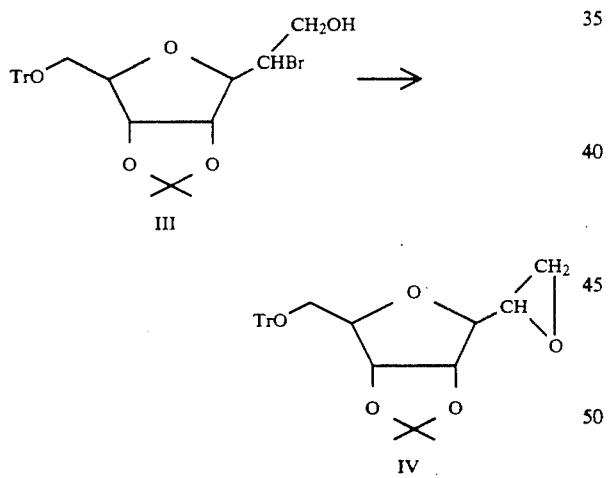

The crude trityl ribose bromohydrin III (4.11 g, 7.63 mmol) was dissolved in 70 mL of DMF and 336 mg (8.4 mmol, 1.1 equiv) of 60% NaH in mineral oil dispersion was added. After stirring overnight at room temperature under N₂, a few mls of H₂O were added to destroy excess NaH. The reaction was concentrated and the oily residue was partitioned between ethyl ether and 10% Na₂CO₃. The ethereal layer was washed several times with H₂O, dried (MgSO₄), filtered and concentrated to provide 3.36 g (96%) of a light yellow oil IV.

$^1$H NMR (200 MHz, CDCl₃ )δ: 1.33, 1.53 (2s, 6H, C(CH₃)₂), 2.68–2.88 (m, 2H CH₂O), 3.09–3.34 (m, 3H, CHOCH₂, CH₂OTr), 3.97 (d of t, 1H), 4.18 (m, 1H), 4.52 (m, 1H), 4.66 (d of d, 1H), 7.18–7.52 ppm (m, 15 H, Tr).

Mass spec FAB Li spike (m+7)=465.

Step C:

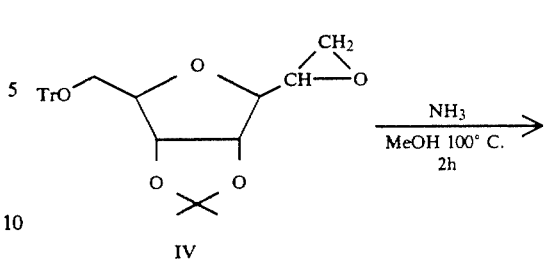

The trityl ribose epoxide IV (2.6 g, 5.67 mmol) was dissolved in 30 mL of MeOH, treated with 80 mL of MeOH saturated with NH₃ and heated in a bomb at 100° C. for 2 hours. The reaction was concentrated to a light amber liquid which was taken up in CH₂Cl₂, filtered with charcoal over Celite and concentrated to give 2.21 g (82%) of amino-alcohol V as an oil. $^1$H NMR (200 MHz, CDCl₃)δ1.34, 1.52 (2s, 6H, C(CH₃)₂), 1.36–1.76 (br s,3H, OH, NH₂), 2.87 (d, 2H, CH₂NH₂), 3.18–3.41 (m, 2H, CH₂OTr), 3.56–3.70 (m, 1H, CHOH), 3.86 (d of t, 1H, H₁ or H₄), 4.14 (m, 1H, H₁ or H₄), 4.54–4.82 (m, 2H, H₂, H₃), 7.16–7.56 ppm (m, 15H, Tr).

Mass spec FAB Li spike m+7=482

Step D:

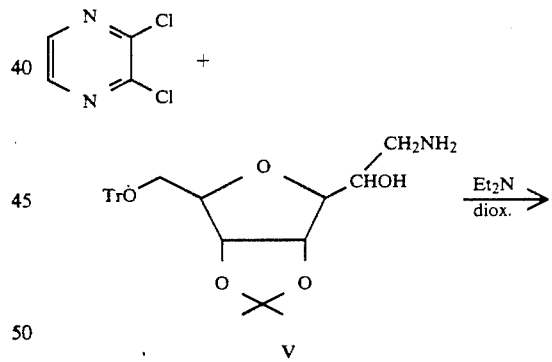

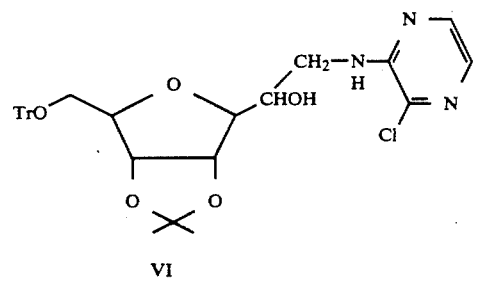

A solution of 2,3-dichloropyrazine (760 mg, 5.03 mmol), 0.89 mL (646 mg, 6.38 mmol) of triethylamine and 2.22 g of the crude V (prepared as described above in Step C) in 10 mL of dioxane was heated at reflux under N₂ overnight. The reaction was concentrated and then partitioned between CH₂Cl₂ and H₂O. The organic layer was dried (MgSO₄) and concentrated to an amber colored oil. Purification on a 200 mL silica gel column (gradient elution 20 to 40% EtOAc in hexanes) gave 1.0 g (1.7 mmol, 40%) of VI as a white solid.

Analysis cal. for C₃₃H₃₅N₃O₅Cl; C:67.40, H:5.83, N:7.14. Found C:67.10, H:5.97, N:6.74

¹H NMR (300 MHz CDCl₃) δ: 1.34, 1.52 (2S, 6H, C(CH₃)₂), 3.04 (d, 1H OH), 3.18–3.62 (m, 3H, CH₂OTr, OH), 3.71–4.19 (m, 4H, CH₂NH₂, H₄', H₁'), 4.79–4.82 (m, 2H, H₂', H₃'), 6.62(t, 1H, NH), 7.18–7.49 (m, 15H, Tr), 7.58 (d of d, 1H), 7.84 ppm (d of d, 1H).

Mass spec FAB Li spike m+7=594, 596.

Step E:

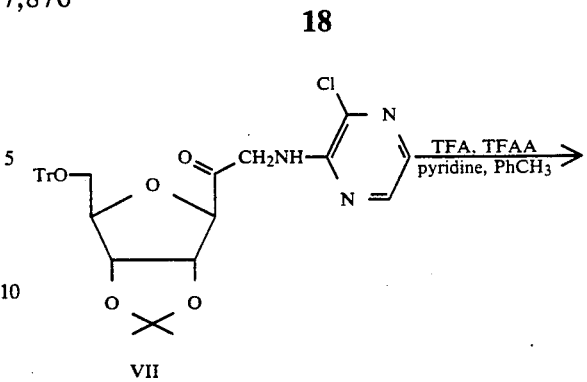

VII

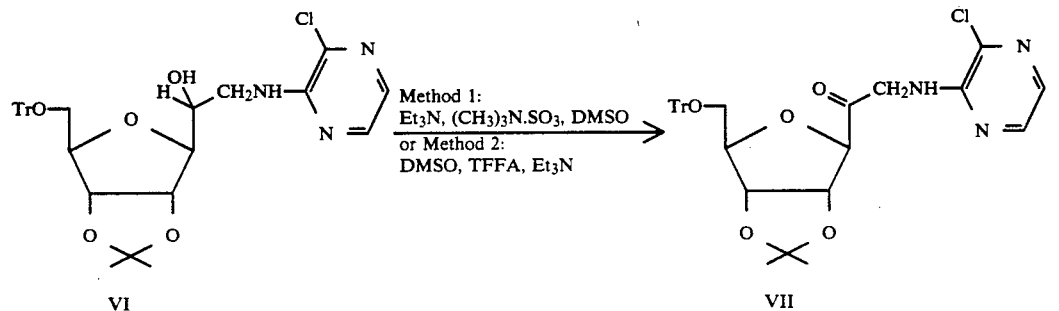

VI                                                           VII

Method 1: The material prepared in Step D, VI (117 mg, 0.2 mmol) was dissolved in 0.5 mL of triethylamine and 0.5 mL of DMSO. The solution was treated with 83.7 mg (0.60 mmol) of trimethylamine-sulfur trioxide complex, stirred overnight at room temperature under N₂ and then heated at 40° C. for 2.5 hours. The reaction was partitioned between CHCl₃ and H₂O. The organic layer was washed again with H₂O, then dried (MgSO₄) and concentrated to 123.2 mg of an amber-colored oil. Purification on a 20 mL silica gel column (20% ethyl acetate in hexanes) gave 52 mg (0.89 mmol, 44%) of VII as a viscous oil.

¹H NMR (200 MHz, CDCl₃) δ: 1.36, 1.54(2S, 6H, C(CH₃)₂), 3.21–3.39 (m, 2H CH₂OTr), 4.36 (m, 1H, H₄), 4.48 (d, 1H, H₁'), 4.56 (m, 2H, CH₂NH), 4,62 (d of d, H₃ or H₂), 5.01 (d of d, H₂ or H₃), 5.76 (m, 1H, NH), 7.15–7.46 (m, 15H, Tr), 7.57 (d, 1H), 7.80 ppm (d, 1H).

Mass spec FAB Li spike (m+7) =592, 594.

Method 2: To 0.21 mL (250 mg, 3.0 mmol) of dry DMSO and 1.5 mL of sieve-dried CH₂Cl2 cooled in a dry ice acetone bath, was added dropwise trifluoroacetic anhydride (0.32 mL, 476 mg, 2.26 mmol) in 1.5 mL of CH₂Cl₂. After 10 minutes, 889 mg (1.51 mmol) of VI in 2.5 mL of CH₂Cl₂ was added dropwise and stirring was continued an additional 10 minutes before allowing the reaction to warm to room temperature. After 50 minutes, 0.6 mL of triethylamine was added dropwise and the reaction was stirred 30 minutes. The reaction was partitioned between Et₂O and H₂O. The ethereal layer was washed again with H₂O, dried (MgSO₄) and concentrated to 849 mg of a yellow solid. Purification on a 100 mL silica gel column (gradient elution 10 to 20% EtOAc in hexanes) gave 490.4 mg (.836 mmol, 55%) of VII as Anal Cal. C:67.63, H:5.50, N:7.17. Found C: 67.87, H:5.74, N:7.06%.

Step F:

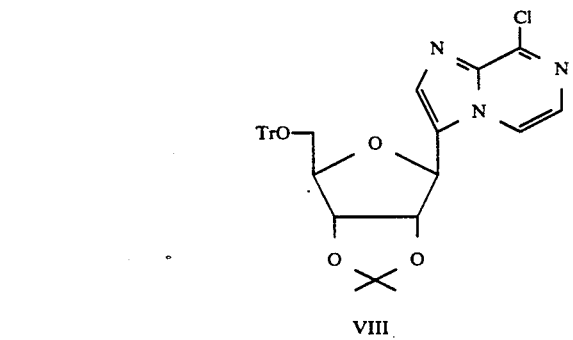

VIII

To 392 mg (0.67 mmol) of VII, prepared as described in Step E, in 5 mL of toluene was added 0.65 mL (634 mg, 8.0 mmol) of pyridine. This solution was cooled in ice and 0.15 mL (222 mg, 2.0 mmol) of trifluoroacetic acid was added. After 30 minutes, 0.66 mL (4.67 mmol) of trifluoroacetic anhydride was added and stirring was continued at 0° C. for 1 hour and then at room temperature overnight. The reaction was diluted with toluene, washed with 10% Na₂CO₃, dried (MgSO₄) and concentrated to 412 mg of oil residue. Purification on a 70 mL silica gel column (gradient elution 20 to 30% ethyl acetate in hexanes) gave 242.6 mg of the product VIII (0.427 mmol, 64%).

Anal: cal. for C₃₃H₃₁N₃O₅Cl; C:69.77, H:5.32, N:7.40. Found. C:69.52, H:5.62, N:7.26.

¹H NMR (300 MHz, CDCl₃) δ: 1.34, 1.55 (2s, 6H, C(CH₃)₂), 3.15–3.30 (m, 2H, H₅', H₅"), 4.31 (d of t, 1H, H₄), 4.82 (d of d, 1H, H₃'), 4.90 (d of d , 1H, H₂'), 5.14 (d , 1H, H₁'), 7.13–7.30 (m, 16H, Tr, C₅-H or C₆-H), 7.68 (s, 1H, C₂-H,) 8.33 ppm (d, 1H, C₅-H or C₆H).

Mass spec FAB (m+1) =568,570.

Step G:

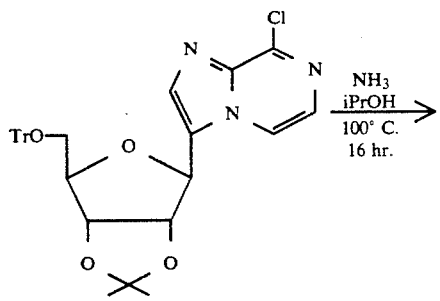

VIII

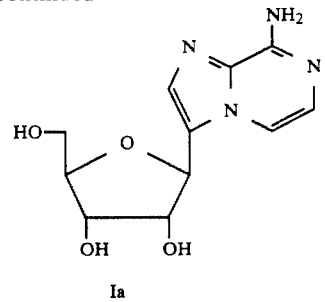

Ia

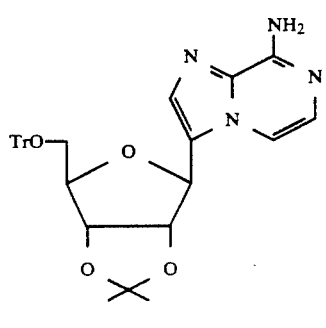

IX

Compound IX (406 mg, 0.74 mmol) was stirred in 12 mL of 90% aq. trifluoracetic acid at room temperature under $N_2$ for 2.5 hours. Absolute ethanol (20 mL) was then added to form TrOEt. Concentration gave a yellow semi-solid which was partitioned between $Et_2O$ and $H_2O$. The aqueous phase was reduced to a smaller volume and passed through a 50 mL anion exchange (AG 1×X2 200–400 mesh) acetate column to give 111.2 mg (.415 mmol, 56%) of Ia as a white solid.

A small portion was recrystallized from EtOH containing a trace of $H_2O$ to give analytically pure material.

Anal. calc. for $C_{11}H_{14}N_4O_4$: C:49.62, H:5.30, N:21.04. Found. C:49.63, H:5.35, N:20.91.

$^1H$ NMR (200 MHz $H_2O$) δ: 3.79 (m, 2H, $H_5'$, $H_5''$), 4.15 (d of t, 1H, $H_4'$), 4.29 (d of d, 1H, $H_3'$), 4.57 (d of d, 1H, $H_2'$), 5.19 (d, 1H, $H_1'$), 7.26 (d, 1H, $C_5$-H or $C_6$-H), 7.66 (s, 1H, $C_2$-H), 7.79 ppm (s, 1H, $C_5$-H or $C_6$-H).

Mass spec (FAB) m+1=267. (EI)=266.

UV data:

MeOH $\lambda_{max}$ 235.5 (29000), $\lambda_{min}$ 285 (6500) NaOH $\lambda_{max}$ 234 (28000), $\lambda_{min}$ 285 (6800) HCl $\lambda_{max}$ 229 (23000), $\lambda_{min}$ 290 (11600).

To 5.05 g (8.9 mmol) of the 8-chloro-3-(ribosyl-)imidazo[1,2-a]pyrazine VIII in 200 mL isopropanol was added 200 mL of ammonia by the high pressure lab. The orange solution was heated at 100° C. for 16 hours. The solution (light yellow) was purged with $N_2$, and then evaporated. The residue was partitioned between $CH_2Cl_2$ and 10% $Na_2CO_3$. The organic layer was dried with $MgSO_4$, filtered and concentrated to give 4.22 g (85%) of IX as a cream-colored solid.

Analysis cal. for $C_{33}H_{32}N_4O_4 \cdot 0.5H_2O$: C: 71.08, H: 5.97, N 10.05. Found: C: 70.98, H: 5.98, N: 9.83.

$^1H$ NMR (300 MHz, $CDCl_3$) δ: 1.38, 1.62 (2s, 6H, $C(CH_3)_2$), 3.30 (m, 2H, $H_5'$, $H_5''$), 4.33 (d of t, 1H, $H_4'$), 4.84 (d of d, 1H, $H_3'$), 4.96 (d of d, 1H, $H_2'$), 5.17 (d, 1H, $H_1'$), 5.43 (s, 2H, $NH_2$), 7.03 (d, 1H, $C_5$ or $C_6$-H), 7.20–7.40 (m, 15H, Tr), 7.50 (s, 1H, $C_2$-H), 7.79 ppm (d, 1H, $C_5$ or $C_6$-H).

Step H:

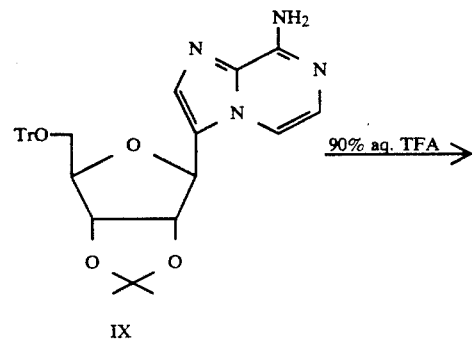

IX

EXAMPLES 2-12

The following examples are prepared by a method analogous to that described in Example 1 using appropriate starting reagents readily available or readily prepared by techniques known in the art. It is understood that in the synthesis of the following examples other protecting groups, known in the art, may be more appropriate than those employed in Example 1.

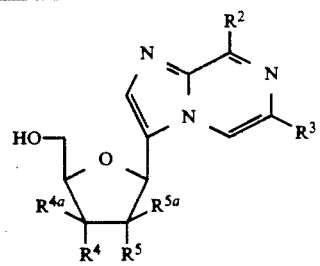

| Example | $R^2$ | $R^3$ | $R^4$ | $R^{4a}$ | $R^5$ | $R^{5a}$ |
|---|---|---|---|---|---|---|
| 2 | $NH_2$ | H | H | OH | OH | H |
| 3 | $NH_2$ | H | OH | H | H | OH |
| 4 | $NH_2$ | H | H | OH | H | OH |
| 5 | $NH_2$ | H | F | H | OH | H |
| 6 | OH | H | OH | H | OH | H |
| 7 | OH | H | H | OH | OH | H |
| 8 | OH | H | OH | H | H | OH |
| 9 | $NH_2$ | $NH_2$ | OH | H | OH | H |
| 10 | OH | $NH_2$ | OH | H | OH | H |
| 11 | H | H | OH | H | OH | H |

-continued

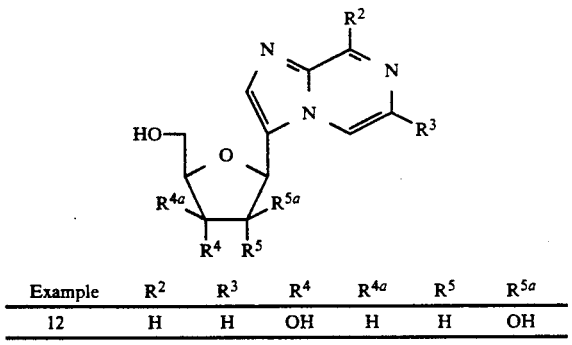

| Example | $R^2$ | $R^3$ | $R^4$ | $R^{4a}$ | $R^5$ | $R^{5a}$ |
|---------|-------|-------|-------|----------|-------|----------|
| 12 | H | H | OH | H | H | OH |

EXAMPLE 13

8-Amino-3-(2,3-dideoxy-β-D-glycero-pent-2-enofuranosylimidazo[1,2-a]pyrazine (Ib)

Step A:

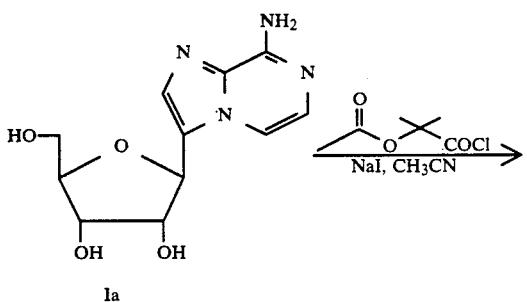

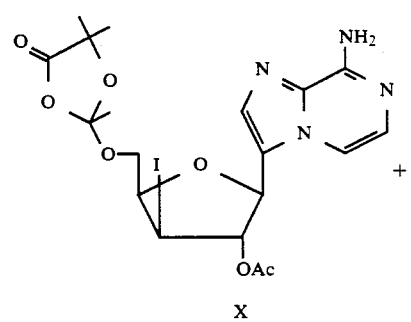

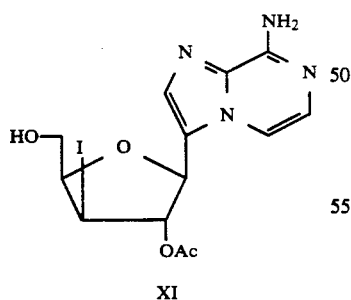

2-Acetoxyisobutyryl chloride (1.3 mL, 9.0 mmol, 1.48 g) was added to a solution of 2.03 g (13.5 nmol) of sodium iodide (dried at 85° C. overnight) in 15 mL of acetonitrile. After 20 minutes, 600 mg (2.25 mmol) of 8-amino-3-(β-D-ribofuranosyl)imidazo[1,2-a]pyrazine Ia, prepared as described in Example 1, was added and stirring was continued an additional 1.5 hour. The reaction was concentrated and then partitioned between EtOAc and aq. NaHCO₃ containing sodium thiosulfate. The organic phase was dried (MgSO₄) and concentrated to 841 mg of mustard-colored solid. Purification on a silica gel* column (gradient elution 0 to 5% MeOH in CH₂Cl₂) gave 136 mg (11%) of X as a white solid and 482.6 mg (51%) of XI as a white solid. *later reaction gave 75% of X using a different batch of silica gel.

X:

Anal. calc. for $C_{19}H_{23}N_4O_7 \cdot 1H_2O$: C: 40.44, H: 4.47, N: 9.93%. Found: C: 40.78, H: 4.27, N: 9.93.

¹H NMR (200 MHz, CDCl₃) δ: 1.50, 1.57 (2s, 6H, C(CH₃)₂), 1.75 (s, 3H, OAc), 2.14 (s, 3H, CCH₃), 3.58-3.94 (m, 3H, H₅', H₅'', H₄'), 4.43 (d of d, 1H, H₃'), 5.12 (d, 1H, H₁'), 5.53 (s, 2H, NH₂), 5.90 (m, 1H, H₂'), 7.36 (d, 1H, C₅ or C₆), 7.64 (m, 1H, C₅ or C₆), 7.69 ppm (s, 1H, C₂-H).

M.S. (FAB) M+1=547.

XI:

¹H NMR (300 MHz, CDCl₃) δ: 1.75 (s, 1H, OH), 2.14 (s, 3H, OAc), 3.79 (m, 2H, H₅', H₅'), 3.92 (d of t, 1H, H₄'), 4.45 (d of d, 1H, H₃'), 5.11 (d, 1H, H₁'), 5.59 (s, 2H, NH₂), 5.94 (d of d, 1H, H₂'), 732 (d, 1H, C₅ or C₆-H), 7.62 (d, 1H, C₅ or C₆-H), 7.68 ppm (s, 1H, C₂-H).

M.S. (FAB) (M+1)=418.

Step B:

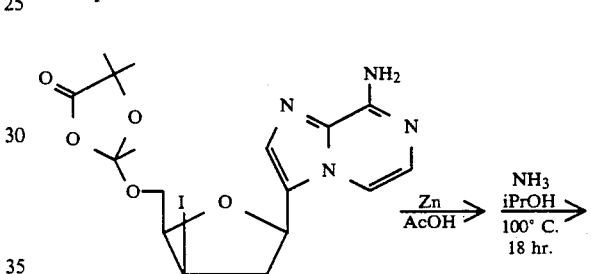

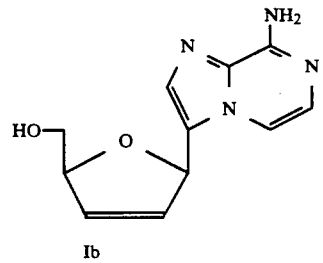

Zinc dust (335 mg, 5.1 mmol) and 59 μL (62 mg, 1.0 mmol) of glacial acetic acid were added with stirring to a solution of 280 mg (0.51 mmol) of acetate X in 15 mL of absolute EtOH. After 20 minutes the suspension was filtered through Celite evaporated to a smaller volume, diluted with EtoAc and washed with 10% Na₂CO₃. The organic layer was dried (MgSO₄) and concentrated to 179.5 mg of an oil which was then dissolved in 10 mL of MeOH saturated with NH₃ and stirred 4 hours in a pressure tube at room temperature. Evaporation under N₂ gave 148.3 mg of white solid. Purification on a 80 mL silica gel column (gradient elution 0 to 20% MeOH in CH₂Cl₂) gave 49.5 mg (41%) of product Ib as a white solid. mp. 219°-221° C.

Anal. calc. for $C_{11}H_{12}N_4O_2 \cdot 0.3H_2O$: C:55.60, H:5.34, N:23.58. Found C:55.54, H:5.20, N:23.25.

¹H NMR (300 MHz, DMSO) δ: 3.32 (m, 1H, OH), 3.43 (m, 2H, H₅', H₅''), 4.79 (m, 1H, H₄'), 6.12 (m, 1H, $H_1'$), 6.22 (m, 2H, $H_2'$, $H_3'$), 6.87 (s, 2H, $NH_2$), 7.22 (d, 1H, $C_5$ or $C_6$-H), 7.39 (s, 1H, $C_2$-H), 7.81 ppm (d, 1H, $C_5$ or $C_6$-H).

Mass spec EI=232.

UV data;

MeOH $\lambda_{max}$ 235 (30410), $\lambda_{min}$ 285 (6850)
NaOH $\lambda_{max}$ 234 (29400), $\lambda_{min}$ 285 (7640)
HCl $\lambda_{max}$ 290 (23250), $\lambda_{min}$ 290 (12260).

EXAMPLES 14–17

The following examples are prepared by a method analogous to that described in Example 13, using appropriate starting materials.

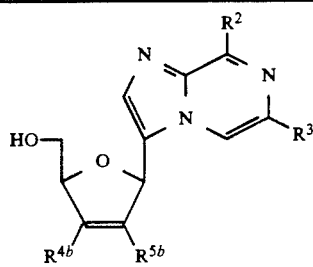

| Example | $R^2$ | $R^3$ | $R^{4b}$ | $R^{5b}$ |
|---|---|---|---|---|
| 14 | $NH_2$ | $NH_2$ | H | H |
| 15 | OH | $NH_2$ | H | H |
| 16 | OH | H | H | H |
| 17 | H | H | H | H |

EXAMPLE 18

8-Amino-3-(2,3-dideoxy-$\beta$-D-glycero-pentofuranosyl)imidazo1.2-a]ovrazine (Ic)

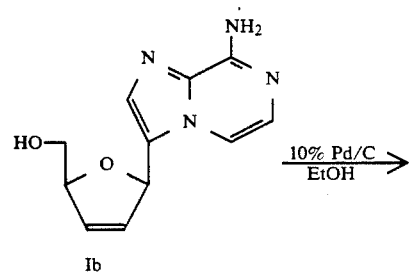

A solution of 28 mg (0.12 mmol) of compound Ib, prepared as described in Example 13, in 10 mL of ethanol containing 30 mg of 10% Pd/c was hydrogenated on the Parr agitator overnight. The suspension was filtered over celite and concentrated to 23.8 mg. Purification on a silica gel column (gradient elution 0 to 8% MeOH in $CH_2Cl_2$) gave 15.1 mg (54%) of product Ic as a white solid.

Anal. calc. for $C_{11}H_{14}N_4O_2 \cdot 0.55$ $H_2O$: C: 54.11, H: 6.23, N: 22.95. Found C: 54.02, H: 5.80, N: 22.57.

$^1H$ NMR (300 MHz, DMSO) $\delta$: 1.81–2.29 (m, 4H, $CH_2CH_2$), 3.40 (m, 2H, $H_5'$, $H_5''$), 4.02 (m, 1H, $H_4'$), 4.73 (t, 1H, OH), 5.14 (t, 1H, $H_1'$), 6.82 (s, 1H, $NH_2$), 7.20 (d, 1H, $C_5$-H or $C_6$-H), 7.48 (s, 1H, $C_2$-H), 7.70 ppm (d, 1H, $C_5$-H or $C_6$-H).

Mass spec. EI=234.

UV data;

MeOH $\lambda_{max}$ 235 (29010), $\lambda_{min}$ 295 (7410)
NaOH $\lambda_{max}$ 234.5 (26540), $\lambda_{min}$ 295 (7410)
HCl $\lambda_{max}$ 229 (20990), $\lambda_{min}$ 290 (12340).

EXAMPLES 19–21

The following examples are prepared by a method analogous to that described in Example 18 using appropriate starting materials.

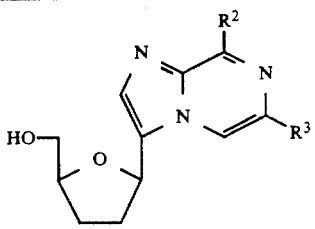

| Example | $R^2$ | $R^3$ |
|---|---|---|
| 19 | $NH_2$ | $NH_2$ |
| 20 | OH | $NH_2$ |
| 21 | H | H |

EXAMPLE 22

8-Amino-3-(3-deoxy-$\beta$-D-glycero-pentofuranosyl)imidazo[1,2-a]pyrazine (Id)

Step A:

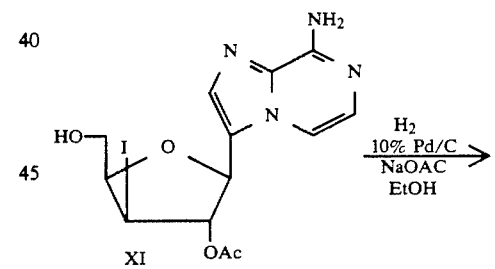

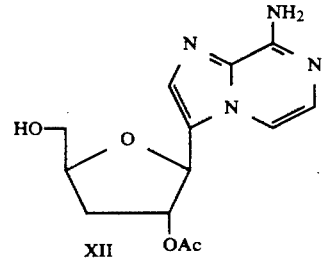

To 83.6 mg (0.20 mmol) of Compound XI, prepared as described in Example 13, Step A, in 5 mL of absolute ethanol containing 25 mg of palladium on carbon was added 20 mg (0.24 mmol) of sodium acetate in 1.0 mL of $H_2O$. The reaction was hydrogenated overnight at 46 psi of hydrogen.

The catalyst was filtered off over celite and the filtrate was concentrated to 109 mg of XII as a yellowish oil. This crude product was used without further purification in Step B.

¹H NMR (200 MHz, CDCl₃) δ: 2.14 (s, 3H, OAc), 2.27–2.45 (m, 2H, H₃′, H₃″), 3.66 (m, 1H), 3.92 (m, 1H), 4.48 (m, 1H, OH), 5.25 (d, 1H), 5.57 (broad s, 3H, NH₂), 7.31 (d, 1H, C₅ or C₆-H), 7.52 (s, 1H, C₅-H), 7.72 ppm (d, 1H, C₅ or C₆-H).

M.S. (FAB) m+1=293.

Step B:

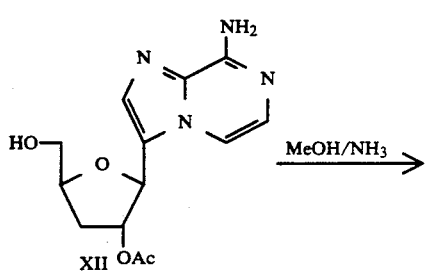

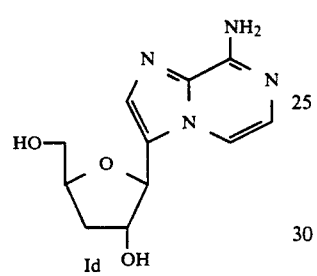

The 2′-deoxyribosylimidazo[1,2-a]pyrazine XII (40 mg, 0.137 mmol) was dissolved in 2 mL of MeOH saturated with NH₃, stoppered and stirred at room temperature overnight. The solution was evaporated under N₂ to an oil which was purified on a silica gel column (5% MeOH in CH₂Cl₂) to give 22 mg (64%) of Id as a pale yellow solid.

¹H NMR (300 MHz, DMSO) δ: 1.84–2.10 (m, 2H, H′₃, H₃″), 3.26–3.52 (m, 2H, H₅′, H₅″), 4.22 (m, 1H, H₄′), 4.43 (m, 1H, H₂′), 4.81 (t, 1H, OH), 4.86 (d, 1H, OH), 5.41 (d, 1H, H₁′), 6.87 (s, 2H, NH₂), 7.25 (s, 1H,), 7,51 (s, 1H), 7.76 ppm (s, 1H).

M.S. (FAB) m+1=251.

EXAMPLES 23-25

The following examples are prepared by a method analogous to that described in Example 22 using appropriate starting materials.

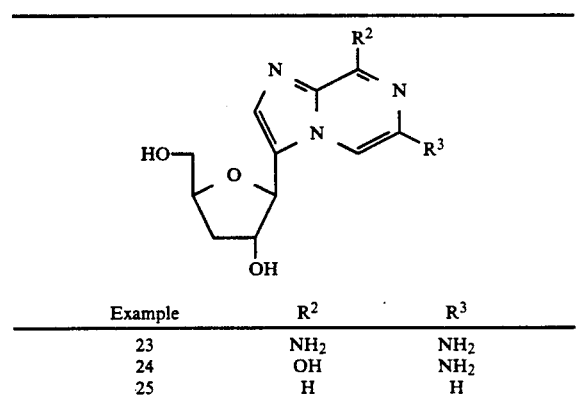

| Example | R² | R³ |
|---------|-----|-----|
| 23 | NH₂ | NH₂ |
| 24 | OH | NH₂ |
| 25 | H | H |

EXAMPLE 26

8-Amino-3-(3-deoxy-β-D-ribofuranosyl)imidazo[1,2-a]pyrazine (Ie)

Step A:

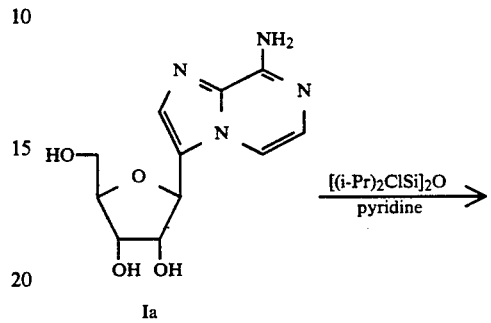

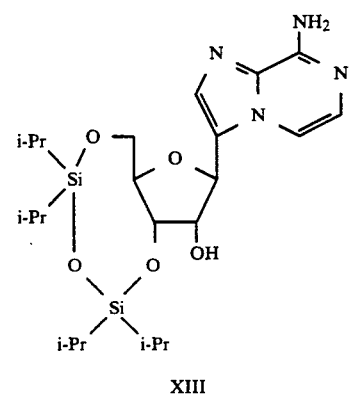

To 400 mg (1.5 mmol) of Compound Ia, prepared as described in Example 1, suspended in 15 mL of dry pyridine under N₂ was added 0.47 mL (474 mg. 1.5 mmol) of 1,3-dichlorotetraisopropyldisiloxane. The reaction was stirred for three days at RT, and then concentrated to a pink solid which was partitioned between EtOAc and cold 0.1N HCl. The organic layer was washed with aq NaHCO₃, dried (MgSO₄) and concentrated to 717 mg of a pink solid. Purification on a silica gel column (3% MeOH in CH₂Cl₂) gave 336 mg (44%) of product XIII as an cream-colored solid.

¹H-NMR (200 MHz CDCl₃) δ: 1.06 (s, 24H, C(CH₃)₂), 1.48 (s, 4H, CH), 3.14 (s, 1H, OH), 3.88–4.18 (m, 3H, H₄′, H₅′, H₅″), 4.31 (m, 1H, H₃′), 4.46 (m, 1H, H₂′), 5.08 (d, 1H, H₁′), 5.50 (s, 2H, NH₂), 7.33 (d, 1H, C₅ C₆-H), 7.55 (s, 1H, C₂-H), 7.61 ppm (d, 1H, C₅ or C₆-H).

Mass spec (FAB): m+1=509.

Step B:

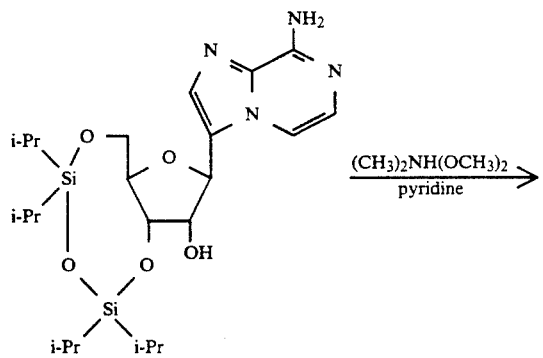

XIII

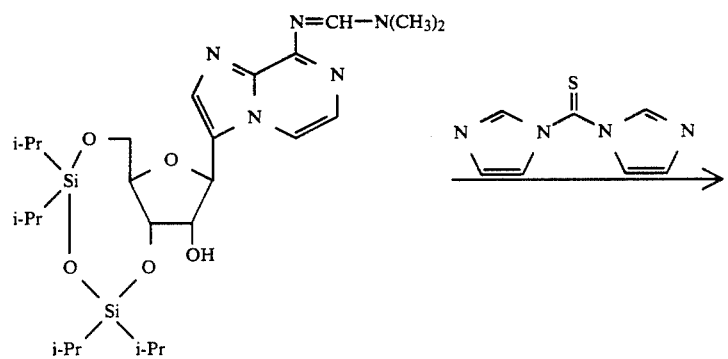

XIV

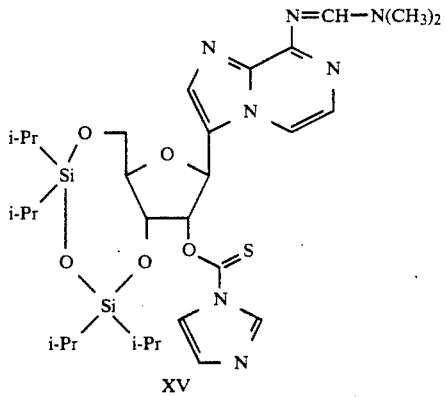

XV

A solution of 180 mg (0.35 mmol) of the protected 2.-hydroxyribosylimidazo[1,2-a]pyrazine XIII and 0.23 mL (1.75 mmol, 210 mg) of dimethylformamide dimethyl acetal in 7 mL of dry DMF was stirred overnight at room temperature. Concentration gave an oil residue of XIV which was treated with 156 mg (0.875 mmol) of diimidazolethiocarbonyl in 5 mL of dry DMF and heated at 80°-90° C. for 3 hours. The reaction was concentrated and then partitioned between EtOAc and H₂O. The organic phase was dried (MgSO₄) and concentrated to an oil residue which was purified on a 100 mL silica gel column (gradient elution 0 to 5% MeOH in CH₂Cl₂) to provide 86.4 mg (0.13 mmol, 37%) of the compound XV.

¹H NMR (300 MHz, CDCl₃) δ: 1.06 (s, 24H, C(CH₃)₂), 1.58 (s, 4H, CH), 3.18, 3.26 (2s, 6H, N(CH₃)₂), 3.98–4.15 (m, 3H), 4.74 (m, 1H), 5.48 (d, 1H, H₁'), 6.17 (m, 1H), 7.08 (s, 1H, imidazole), 7.50 (d, 1H, C₅-H or C₆-H), 7.68 (s, 1H, imidazole), 7.70 (s, 1H, C₂-H), 7.80 (d, 1H, C₅-H or C₆-H), 8.39 (s, 1H, imidazole), 8.73 ppm (s, 1H) N=CH—N.

Step C:

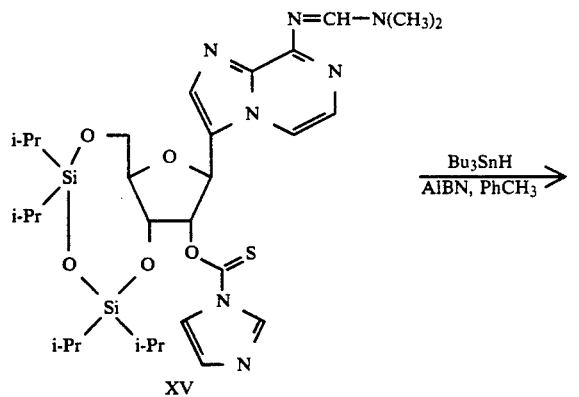

XV

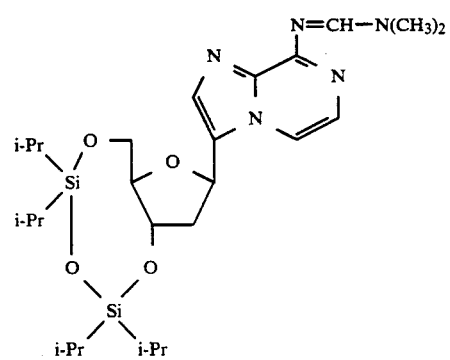

XVI

Compound XV (83.6 mg, 0.126 mmol) was dissolved in 20 mL of toluene and heated at 80° C. in an oil bath. A mixture of 170 mL (183 mg, 0.63 mmol) of tri-n-butyl-tin hydride and 17 mg (0.100 mmol) of AIBN in 0.5 mL of toluene was added dropwise and heating was continued for 3 hours. The reaction was concentrated and purified on a silica gel column (2% MeOH in $CH_2Cl_2$) to give 69.5 mg of a yellow oil which was 70% of the desired product XVI by NMR.

$^1$H NMR (300 MHz, CDCl$_3$) δ: 1.06 (s, 24H, C(CH$_3$)$_2$), 1.58 (m, 4H, CH), 2.38–2.61 (m, 2H, H$_2'$, H$_2''$), 3.16, 3.24 (2s, 6H, N(CH$_3$)$_2$), 3.75 (m, 1H, H$_4'$), 3.90–4.17 (m, 2H, H$_5'$, H$_5''$), 4.62 (m, 1H, H$_3'$), 5.37 (t, 1H, H$_1'$), 7.47 (d, 1H, C$_5$ or C$_6$-H), 7.54 (s, 1H, C$_2$-H), 7.79 (d, 1H, C$_5$ or C$_6$-H), 8.70 ppm (s, 1H, =CH—N).

Step D:

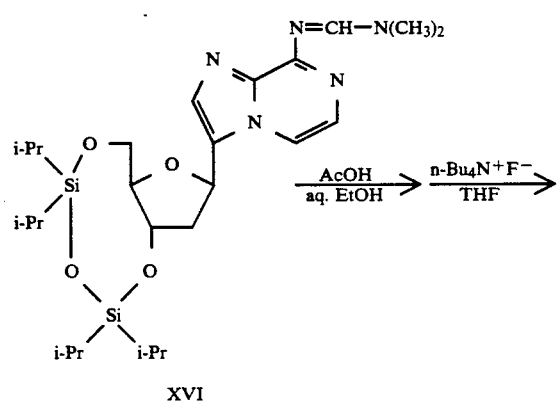

XVI

-continued

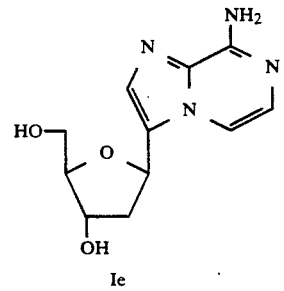

Ie

Compound XVI (66.5 mg 0.12 mmol) was dissolved in a mixture of 1.5 mL ethanol, 1.5 mL H$_2$O and 1.5 mL acetic acid and stirred at room temperature for 3 days. The reaction was concentrated, azeotroped several times from EtOH and then treated with 0.24 mL of 1M TBAF in THF and heated under N$_2$ in an oil bath at 75° C. After 3 hours the reaction was concentrated to give an oily residue which was purified on a silica gel column (gradient elution 0 to 10% MeOH in CH$_2$Cl$_2$) to give 14.7 mg (49%) of compound Ie.

$^1$H NMR (300 MHz, D$_2$O) δ: 2.33–2.74 (m, 2H, H$_2'$, H$_2''$), 3.06–3.40 (m, 2H, H$_5'$, H$_5''$), 4.15 (m, 1H), 4.58 (m, 1H), 5.58 (m, 1H), 7.33 (d, 1H, C$_5$ or C$_6$-H), 7.68 (s, 1H, C$_2$-H), 7.86 ppm (d, 1H, C$_5$ or C$_6$-H).

Mass spec FAB=m+1=251.

EXAMPLES 27–29

The following examples are prepared by a method analogous to that described in Example 25 using appropriate starting materials.

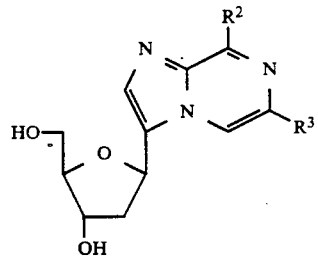

| Example | R$^2$ | R$^3$ |
|---|---|---|
| 27 | NH$_2$ | NH$_2$ |
| 28 | OH | NH$_2$ |
| 29 | H | H |

What is claimed is:

1. A compound of the Formula I:

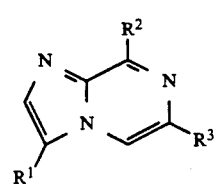

I wherein
R$^1$ is selected from
a)

and
b)

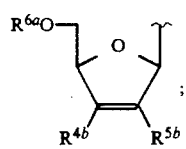

R² and R³ are independently: hydrogen, —NH₂ or
—OH;
R⁴, R⁴ᵃ, R⁵ and R⁵ᵃ are independently: hydrogen,
fluorine or hydroxyl;
R⁶ is:
 a. hydrogen,
 b. —C(O)R⁷,
 c.

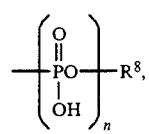

or
 d. R⁶ may be combined with R⁴ to form a cyclic
    phosphate;
R⁴ᵇ and R⁵ᵇ are hydrogen or C₁-C₄ lower alkyl;
R⁶ᵃ is
 a. hydrogen,
 b. —C(O)R⁷, or
 c.

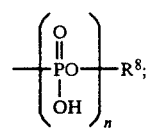

R⁷ is lower alkyl,
 R⁸ is hydrogen or lower alkyl;
 n is 1 to 3;
or a pharmaceutically acceptable salt thereof.

2. The compound of claim 1 wherein R¹ is

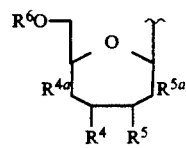

and R⁴, R⁴ᵃ, R⁵, R⁵ᵃ, and R⁶ are as defined in claim 1.

3. The compound of claim 1 wherein R¹ is

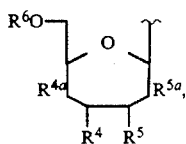

and R⁴ᵇ, R⁵ᵇ, and R⁶ᵃ are as defined in claim 1.

4. The compound of claim 1 of Formula Ia:

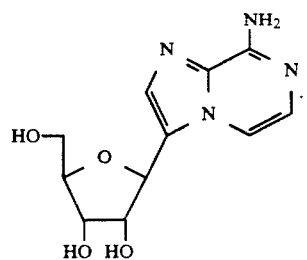

5. The compound of claim 1 of Formula Ib:

Ib

6. The compound of claim 1 of Formula Ic:

Ic

7. The compound of claim 1 of Formula Id:

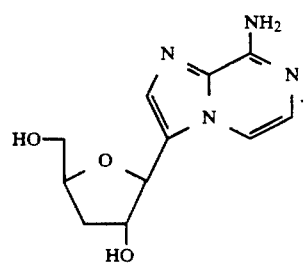

8. The compound of claim 1 of Formula Ie:

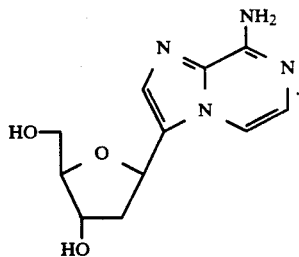

Ie

9. An immunosuppressive pharmaceutical composition comprising an effective amount of a compound of claim 1 and a pharmaceutically acceptable carrier.

10. A method for inhibiting HIV in a cell culture exposed to HIV, which comprises applying an HIV-inhibitory effective amount of the compound of claim 1 to said culture.

11. A method for treating inflammation in a mammal in need of such treatment which comprises administering to said mammal an anti-inflammatory effective amount of a pharmaceutical composition which comprises an anti-inflammatory effecitve amount of the compound of claim 1 and a pharmaceutically acceptable carrier.

12. A method for treating inflammation in a mammal in need of such treatment which comprises administering to said mammal an anti-inflammatory effective amount of a compound of claim 1.

* * * * *